United States Patent
Robb et al.

(10) Patent No.: US 10,161,942 B2
(45) Date of Patent: Dec. 25, 2018

(54) CROSSMATCHING BLOOD SAMPLES

(71) Applicant: QBD (QS-IP) LIMITED, St. Helier (GB)

(72) Inventors: Janine Scott Robb, Midlothian (GB); David Cooper Robson, Midlothian (GB); Neil Kevin Renault, Midlothian (GB); Christopher Robert James Claxton, Midlothian (GB)

(73) Assignee: QBD (QS-IP) LIMITED, St. Helier, Jersey (GB)

(*) Notice: Subject to any disclaimer, the term of this patent is extended or adjusted under 35 U.S.C. 154(b) by 148 days.

(21) Appl. No.: 15/117,035

(22) PCT Filed: Feb. 6, 2015

(86) PCT No.: PCT/GB2015/050338
§ 371 (c)(1),
(2) Date: Aug. 5, 2016

(87) PCT Pub. No.: WO2015/118347
PCT Pub. Date: Aug. 13, 2015

(65) Prior Publication Data
US 2017/0168075 A1 Jun. 15, 2017

(30) Foreign Application Priority Data
Feb. 7, 2014 (GB) .................... 1402174.5

(51) Int. Cl.
*G01N 33/80* (2006.01)
*G01N 33/555* (2006.01)

(52) U.S. Cl.
CPC ........... *G01N 33/80* (2013.01); *G01N 33/555* (2013.01); *G01N 2333/705* (2013.01)

(58) Field of Classification Search
None
See application file for complete search history.

(56) References Cited

U.S. PATENT DOCUMENTS

| 2007/0172899 A1 | 7/2007 | Graham et al. |
| 2010/0041565 A1 | 2/2010 | Robb et al. |
| 2013/0130280 A1 | 5/2013 | Fauconnier et al. |

FOREIGN PATENT DOCUMENTS

| WO | WO 95/30904 | 11/1995 |

OTHER PUBLICATIONS

Morelati et al. ("New Technology in Immunohaematology" 2007 Blood Transfusion vol. 5, p. 58-65 (Year: 2007).*
Garratty et al. ("Advances in Red Blood Cell Immunology from 1960-2009" 2010 Transfusion vol. 50, p. 526-535) (Year: 2010).*
Bouix et al. ("An Original and Innovative Method for Blood Group Serology" 2008 Transfusion vol. 48, p. 1878-1885) (Year: 2008).*
Moore et al., Solid phase indirect anti-human globulin test for identification of red blood cell antibodies in human sera, Transfusion, Jan. 1, 1982, vol. 22, No. 6, p. 540.
Petrik, Microarrays and Blood Diagnostics, Chapter 15, Bioarrays: From Basics to Diagnostics, 2007 Humana Press, pp. 215-230.
International Search Report and Written Opinion for corresponding PCT Application No. PCT/GB2015/050338, dated Apr. 23, 2015, 14 pages.

* cited by examiner

*Primary Examiner* — Changhwa J Cheu
(74) *Attorney, Agent, or Firm* — Myers Bigel, P.A.

(57) ABSTRACT

The present invention provides novel methods for the detection of antibodies, in particular, blood group antibodies. The methods of this invention may be applied to pre-transfusion blood compatibility testing for the detection of incompatibility between donor units (comprising donor red blood cells (erythrocytes)) and a recipient.

29 Claims, 10 Drawing Sheets

Figure 1:
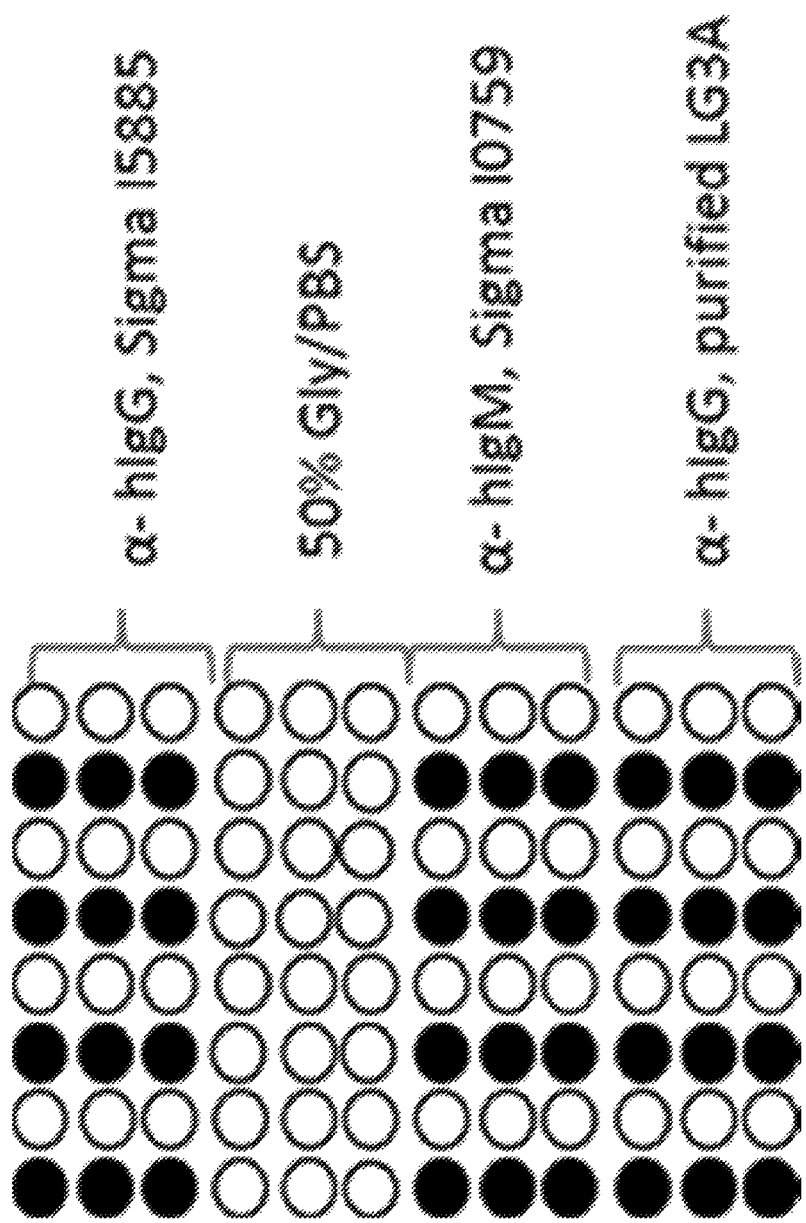

| AHG result | Slide CM60 – in tube | | Slide CM61 – on glass slide |
|---|---|---|---|
| na | | Z441 | |
| 2+ | | OR$_1$r | |
| 3+ | | OR$_1$R$_1$ | |
| 2+ | | OR$_2$R$_2$ | |
| na | | Blank | |
| -ve | | Orr | |
| -ve | | Orr | |
| na | | Blank | |

Figure 4

CROSSMATCHING BLOOD SAMPLES

RELATED APPLICATIONS

This application is a 35 U.S.C. § 371 national phase application of PCT International Application No. PCT/GB2015/050338 having an international filing date of Feb. 6, 2015, which claims priority to GB Application No. 1402174.5, filed Feb. 7, 2014, the disclosures of which are incorporated by reference herein in their entireties. The above PCT International Application was published in the English language as International Publication No. WO 2015/118347 A1.

FIELD OF THE INVENTION

The present invention provides novel methods for the detection of antibodies—in particular, blood group antibodies. The methods of this invention may be applied to pre-transfusion blood compatibility testing for the detection of incompatibility between donor red blood cells (erythrocytes) and recipient plasma.

BACKGROUND OF THE INVENTION

Crossmatch testing is part of the pre-transfusion compatibility procedures performed in blood transfusion laboratories: the tests include ABO and RhD grouping, antibody screening, antibody identification, direct or indirect crossmatching.

It is routine for transfusion service laboratories to perform ABO and RhD blood typing, reverse ABO typing, and irregular antibody screening on all patients. This is performed in order to provide blood which is ABO and RhD compatible and lacking the blood group antigen to which the patient has an antibody; this will prevent or reduce the risk of transfused donor erythrocytes being destroyed by the patient. In the event of a positive antibody screen, an antibody identification investigation will be performed to identify the antibody present—often called an irregular blood group antibody as its presence is not expected, unlike regular blood group antibodies such as anti-A or anti-B, formed without known antigen stimulation and due to environmental factors. An antibody screen or identification involves the use of the patient's plasma/serum tested against a panel of specially selected erythrocyte samples, which carry the clinically significant blood group antigens against which irregular blood group antibodies are directed.

If an antibody screen returns a negative result, computer matching may be used to select suitable units for transfusion to the patient. This can occur only where appropriate validation and adherence to guidelines gives the laboratory the authorisation to do so. If however, the antibody screen is positive and an antibody is present, further compatibility tests must be carried out. This will include full antibody identification investigation and crossmatching. Compatibility tests, here referred to as crossmatching, include testing of the patient's plasma/serum against potential donor erythrocyte units.

Donor erythrocyte units should be selected as the same ABO and Rh group as the patient, and negative for the blood group antigen to which the patient has an antibody. Often this will involve blood typing of donor erythrocyte units to find those which are negative for the antigen in question, although depending on the routine testing regime of the transfusion service this testing may have been performed at the time of donor unit testing.

Conventionally, compatibility testing has been carried out as an agglutination test in a test tube. More recently this test has also been carried out using solid-phase microplate and column agglutination technologies (aka Gel, CAT). The test however, is still somewhat cumbersome requiring multiple wash steps and centrifugation. The test follows the principles of indirect antiglobulin testing (IAT, IAGT); an erythrocyte suspension is allowed to incubate with a sample of plasma/serum/blood typing reagent or control. During this first step, if an antibody is present and the antigen to which it is specific is also present on the erythrocytes, binding of antibody to antigen will occur—this step is called sensitisation. Following sensitisation, wash steps are required to separate unbound antibody in solution, from the sensitised erythrocytes. Following this wash step, an anti-human globulin reagent is added; this contains anti-human IgG antibodies and often anti-C3. If antibody has sensitised the erythrocytes the anti-human IgG will bind to the IgG antibody on the erythrocytes causing haemagglutination. In conventional testing, IgM incompatibility is identified through direct haemagglutination, without the sensitisation pre-step. Haemagglutination is the end point used for detection of a sensitisation reaction. Failure to remove unbound IgG can lead to neutralisation of the anti-human IgG present in the anti-human globulin reagent and potentially lead to a false negative result. This is usually controlled by the addition of IgG sensitised cells to all negative IAT tests; here a positive result shows that the anti-human IgG is available and has not been neutralised, and therefore adequate washing/removal of unbound antibody has occurred. If the test is negative it may demonstrate that the binding regions of the anti-human IgG are blocked, and most likely 'neutralised', and it may be concluded that the test is invalid due to insufficient washing or unbound antibody removal.

Current state-of-the-art includes commercially available systems such as Immucor Capture-R, and BioRad ID-System and Ortho Clinical Diagnostics BioVue and ID-MTS systems, and although many other variations are now available they are very similar in principle to the systems mentioned above. Solid phase systems, such as the Immucor Capture-R Select involve binding of the donor erythrocytes to a microplate well, followed by incubation with patient plasma/serum, wash steps and then finally addition of indicator cells (cells coated with anti-D and a level of anti-IgG) so where antibody has sensitised the bound donor erythrocytes the anti-IgG on the indicator cells will also bind to the donor antibody bound to the donor erythrocytes. In this example, wash steps are required to remove unbound antibody. Column agglutination techniques use a microtube containing anti-human IgG (and/or anti-C3) and use a well above the microtube to allow incubation/sensitisation of donor cells with patient plasma/serum, before centrifugation through the column containing anti-human IgG. In this case centrifugation is used to separate the unbound antibody, as the erythrocytes are forced through the microtube by centrifugation leaving unbound antibody in the well above the microtube as the centrifugal force is appropriate to force cells down but will not be sufficient to allow unbound antibody into the anti-IgG column.

Current systems as described above, use either centrifugation and/or wash steps to separate the sensitised erythrocytes from unbound antibody. Such procedures are time and reagent consuming and thus render prior art processes less suitable for rapid high-throughput screening.

The presence of antigens (including blood group antigens) on the surface of erythrocytes forms the basis of many immunological tests including, for example blood typing assays which use non-agglutination protein microarrays, in which an immobilised antibody binds to an antigen on the surface of the erythrocytes, and the presence of erythrocytes so immobilised is detected (J S Robb et al 2006). Antibody microarray technology can also be used to phenotype erythrocytes by detecting complex mixtures of antigens on cell surfaces (C J Campbell et al 2006). The antigens expressed by erythrocytes are both sugar antigens, which tend to be well presented and easily accessible, and protein peptide antigens, which are epitopes of transmembrane proteins and therefore buried and held more closely to the cell surface, and these were successfully differentiated using the correct choice of antibodies.

SUMMARY OF THE INVENTION

The present invention provides novel methods for the detection of antibodies—in particular, blood group antibodies. The methods of this invention may be applied to pre-transfusion blood compatibility testing for the detection of incompatibility between donor units (comprising donor red blood cells (erythrocytes)) and a recipient.

Red blood cells can appear "foreign" to a host immune system if they express antigens not found on the red blood cells of that host. It is for this reason that blood must be carefully crossmatched before it is transfused. For example, some red blood cells express A type antigens; blood in which the red blood cells express the A blood group antigen is referred to as blood group "A". Other blood groups include "B" (where the erythrocytes express the "B" blood group antigen), "AB" (where the erythrocytes express both the A and B blood group antigens) and O (where the erythrocytes do not express either the A or B blood group antigens). As explained in more detail below, an incompatibility between donor red blood cells (erythrocytes) and a recipient depends upon the presence of antibody in the recipient plasma which binds to antigens present on red blood cells. Incompatibility testing may be referred to as "crossmatching".

A complete crossmatch depends not only on the presence or absence of anti-A or anti-B antibodies in plasma, but also on other antibodies with affinity for other antigens expressed by red blood cells/erythrocytes (including, but not limited to, Rh, Kell and the like).

If incompatible donor blood is transfused, the recipient's immune system (specifically those circulating antibodies with affinity for the antigens present on the "foreign", transfused, blood) will "attack" the incompatible blood and the transfusion may fail. Moreover, the mass destruction of the donor blood can induce inappropriate and/or exaggerated immune responses and the clotting system cascades. Shock, kidney failure and even death may occur following an incompatible blood transfusion.

When a sample of recipient plasma is incubated with an incompatible source of red blood cells, antibodies in the plasma with specificity for the "foreign" red blood cell antigens, bind to those antigens and "coat" the red blood cells. This process is known as sensitisation and red blood cells with antibody bound to surface antigen are referred to as "sensitised erythrocytes" or "sensitised red blood cells".

The inventors have noted that red blood cells (erythrocytes) sensitised with antibody (protein) can withstand the processing steps required to execute an immunological assay. Indeed, sensitised red blood cells (erythrocytes) subjected to immunological assays and other processing procedures may remain 'sensitised' (coated) with antibody throughout the various incubation and washing steps. In view of the above, the process of sensitisation can be exploited as the basis of an immunological crossmatching test.

In a first aspect, the invention provides a method of crossmatching blood samples, said method comprising:
    providing plasma or serum from a first blood sample;
    contacting the plasma sample with red blood cells from a second blood sample to provide a plasma/red blood cell mix;
    incubating the plasma/red blood cell mix under conditions which permit sensitisation of the red blood cells;
    separating the red cells (some or all of which of which, may or may not be sensitised) from a liquid phase; and
    contacting the sensitised red cells with an agent capable of binding antibodies;
    wherein the separation of the sensitised red cells from a liquid phase takes place without centrifugation and the detection of sensitised red blood cells bound to the agent capable of binding antibodies indicates that the donor blood is incompatible with the blood of the intended recipient.

It should be understood that the sensitisation of the red blood cells occurs through binding between (for example, anti-blood group antigen) antibodies present in the plasma and antigens (for example blood group antigens) of the red blood cells.

Plasma or serum for use in this invention may be prepared from whole blood using any suitable or standard preparation protocol. Where the method of this invention is a method for crossmatching blood, the plasma and/or serum may be provided by, or derived from, a patient who is to receive a blood transfusion. In order to prepare plasma for use, whole blood may be collected into anticoagulant-treated tubes. Red blood cells and platelets are removed or separated by centrifugation and the resulting supernatant is designated plasma. A plasma sample for use in this invention may comprise, for example, a volume of about 10 μL to about 1 mL. For example, about 100 μL, 150 μL, 160 μL, 200 μL, 250 μL or 300 μL of plasma may be used. To prepare serum for use, whole blood may be collected and allowed to clot for a period of time. Again, red blood cells and platelets are removed by centrifugation and the resulting supernatant is designated serum. Plasma and/or serum for use in the methods of this invention may be diluted with a suitable buffer or diluent prior to use. Plasma and/or serum may be prepared for use as a 1:1, 1:2, 1:3, 1:4, 1:5, 1:6, 1:7, 1:8, 1:9 or 1:10 dilution. Suitable diluents may include, for example, phosphate buffered saline (PBS) and/or low ionic strength solution (LISS).

Red blood cells for use in this invention may be derived from any suitable source of whole blood. Where the method is a method for crossmatching blood for transfusion, the red cells may be obtained from a source of donor blood which is intended for use. Donor blood may be collected and stored in flexible plastic bags. The bags may contain compounds and chemicals (for example sodium citrate, phosphate, dextrose, and sometimes adenine) which prevent the blood from clotting and facilitate storage. The tubing through which blood passes into the storage bag may be segmented after collection to provide "pigtail" sections which contain small volumes of blood. These small "pigtail" volumes of donor blood are suitable for use in crossmatching assays, including the assays of this invention. Small volumes of whole blood may be provided as a source of red blood cells for use in the assays of this invention. For example, about 1 ul to about 500 ul or red blood cells may be used. The crossmatching assays of this invention may use about 10 μL, 20 μL, 30 μL, 40 μL, 50 μL, 60 μL, 70 μL, 80 μL, 90 μL or 100 μL of whole blood. Prior to use, the red blood cells may be diluted with any suitable diluent or buffer.

The plasma and/or serum and red blood cells may be mixed to provide a plasma/red blood cell mixture. For convenience, the plasma/serum and red blood cell mix will be referred to as a "cell mix". The cell mix may be further diluted using a suitable buffer or medium. For example, the cell mix may be diluted using low ionic strength solution (LISS). Suitable dilutions of the cell mix may include, for example 1:1, 1:2, 1:3, 1:4; 1:5 or 1:6 dilutions with buffer (LISS for example).

The (optionally diluted) cell mix, may be incubated under conditions which permit antibodies present in the plasma or serum (for example anti-blood group antigen antibodies) to interact with and bind to antigens present on the surface of the red blood cells. As mentioned above, red blood cells to which antibodies, for example, anti-blood group antigen antibodies have bound, are referred to as "sensitised" red blood cells. Thus, the incubation of the cell mix may be conducted under conditions suitable to permit or allow the formation of sensitised red blood cells. Further, the conditions may include a predetermined time and/or a predetermined temperature. For example, the cell mix may be incubated at about 30-40° C., for example 37° C. and/or for about 10 seconds to several hours. The cell mix may be incubated at about 37° C. for about 5 min, about 10 min, about 15 min, about 20 min, about 25 min or about 30 min.

The cell mix may be prepared and/or incubated in or on any suitable substrate, vessel, tube, plate (including multi-well plates) and/or slide. The cell mix may be prepared and/or incubated on or in glass and/or plastic substrates, vessels, tubes, plates and/or slides. Substrates, vessels, plates and/or slides (whether glass, plastic or comprising some other material) may be coated and/or blocked to prevent or reduce non-specific binding between plasma/serum and/or whole blood components and the material of the substrate, vessel, tube, plate or slide.

For reasons outlined above, crossmatching assays must be both sensitive and specific. In particular it is important that instances of false positive and/or negative results are brought to within certain tolerance levels or occur at no greater frequency than what would be regarded as acceptable. One of skill will appreciate that in the case of a crossmatching assay, false negative results would suggest that donor blood is compatible when, in fact, the donor blood may be incompatible. In a method of this invention, a false negative result may occur if the process used to detect sensitised red blood cells becomes blocked, neutralised or otherwise inhibited. The process used to detect sensitised red blood cells may require a binding agent (for example an antibody) that has affinity for antibodies. Binding agents of this type may be blocked, neutralised and/or prevented from interacting with sensitised red blood cells by antibody present in plasma and/or serum.

As such, the presence of unbound plasma/serum antibodies with specificity for red blood cell (erythrocyte) antigens present in the cell mix must be (substantially) removed from the remainder of the methods of this invention.

Typically, the occurrence of false negative results in immunological (including crossmatching) assays is prevented by frequent washing and/or centrifugation steps. This ensures that after any initial period of incubation between a plasma/serum sample and a source of red blood cells (to produce sensitised red blood cells), any unbound antibodies present in the plasma/serum are not carried through to the final stages of the assay where they can neutralise the binding agents (for example antibodies) used to detect the sensitised red blood cells. Washing steps facilitate the removal of unbound antibody from an assay whereas centrifugation affects the separation of unbound antibodies in liquid phase from those which have bound their target.

While washing and/or centrifugation steps represent effective means to reduce instances of false negative and/or positive results in immunological assays, including assays of the type described herein, they are time consuming and increase the amount of peripheral equipment required to complete the assay.

The present invention represents an improvement as it provides a sensitive, specific, accurate and rapid assay for crossmatching blood, which assay achieves a rate or level of false positive and/or false negative results comparable with prior art crossmatching assays and tests but with reduced use of washing and/or centrifugation steps.

This is, in part, achieved by conducting the cell mix incubation step under conditions which permit the separation of the red cell component of the cell mix from the liquid phase of the cell mix. For example, the incubation may be conducted under conditions which facilitate the settling (under gravity) of the cells (some, all or none of which may be sensitised) to form, for example, a pellet. The settling of the cells and/or formation of a pellet may leave a liquid phase or supernatant comprising antibodies which have not bound to red blood cell antigens and other plasma or serum components. The formation of a pellet of red blood cells permits easy separation of the red blood cells (or a sample thereof) from the liquid phase (or supernatant) such that the remainder of the assay can be conducted on the (perhaps sensitised) red blood cell component and in the absence of plasma or serum components which, as described above, may lead to false negative and/or false positive results.

The methods of this invention and in particular the cell mix incubation step, avoids the use of centrifugation to form the cell pellet or to separate the red cells (some, all or none of which may be sensitised) from the liquid phase of the cell mix and any unbound antibody. Rather, the red blood cells are allowed to separate from the liquid phase and settle over time and/or under gravity. This may result in the formation of a natural red blood cell pellet or clump. Once a pellet of red blood cells has formed and settled, the user may perform either or both of the following actions. The supernatant may be removed leaving only the red blood cells, some of which may have become sensitised by anti-blood group antigen antibodies during the cell mix incubation step. Additionally or alternatively, a settled or pelleted red blood cell clump or a sample thereof, may be removed. The remainder of the assay is then performed either on those red blood cells remaining after removal of the supernatant or the red blood cells removed from the red cell mix.

The inventors have surprisingly found that once the red blood cells have pelleted and/or settled, removal of the liquid phase/supernatant by, for example pipetting or decanting or removal of the settled/pelleted red blood cells (or a sample thereof) by, for example, suction (aspiration), is sufficient (and no additional washing is required before the cells are resuspended in buffer for application of the binding agents) to ensure that the methods of this invention exhibit a similar, comparable (or perhaps even better) occurrence or level of false positive and/or negative results as observed in (or with) prior art assays. Thus, without wishing to be bound by theory, it is suggested that removal of the supernatant or liquid phase or removal of the settled/pelleted red blood cells (or a sample thereof) is sufficient to remove unbound plasma/serum antibody from the assay to such an extent that the binding agents used in the detection of sensitised red blood cells, do not become neutralised.

The red blood cells for use in the remainder of the method of this invention may be re-suspended in a suitable buffer before being brought into contact with agents capable of binding antibodies. A suitable red blood cell re-suspension buffer may comprise, for example bovine serum albumin and/or LISS.

The optionally re-suspended red blood cells (some of which may have become sensitised) are contacted with agents capable of binding antibodies. For example, if the method of this invention is conducted using human samples (human plasma and human donor blood) the binding agents capable of binding antibodies should be capable of binding human antibodies. Binding agents for use in this invention may be antibodies or antigen binding fragments thereof, with specificity for one or more antibody isotypes. For example, a single antibody type specific to a single antibody isotype (immunoglobulin G, M, A, E or D for example) or a plurality of different antibodies each with specificity for a different antibody isotype.

The agent capable of binding sensitised red blood cells may itself be an antibody or an antigen binding fragment thereof, which exhibits specificity and/or affinity for one or more other antibodies coating (sensitising) a red blood cell. Additionally, or alternatively, other specifically reactive binding agents, such as for example, small molecule antibody mimetics, aptamers, nucleic acid ligands, or receptors from other cells which are capable of binding sensitised red blood cells, may be used. Lectins may also be employed. For simplicity reference hereinafter will be made to binding agents and "antibodies", but this should not be construed as limiting.

It will be appreciated that the choice of binding agent (for example antibody) used in the methods of this invention will depend on the nature of the antibodies coating (sensitising) the red blood cells. For example, the binding agent may be any agent capable of binding a plasma/serum antibody or any other component present in plasma or serum which might sensitise (bind to) a red blood cell. For example, the binding agents for use in this invention may comprise agents capable of binding immunoglobulin and/or complement factors. In general the binding agents used would correspond to those used in conventional DAT or IAGT testing i.e. at least anti-IgG$_1$, anti-IgG$_3$, and anti-Complement (C3) or a broad spectrum anti-human IgG, of either monoclonal or polyclonal source. Advantageously, anti-IgG$_2$ and IgG$_4$ antibodies may be used. If desired other antibodies could also be included such as for example, anti-light chain λ, or anti-light chain κ antibodies.

The methods of this invention may use polyclonal and/or monoclonal antibodies. Polyclonal antibodies are heterogeneous populations of antibody molecules derived from the sera of animals immunised with an antigen, or an antigenic functional derivative thereof. For the production of polyclonal antibodies, host animals for example rabbits, sheep, pigs, etc., can be immunised by injection with a specific antigen optionally supplemented with adjuvants.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein (1975), Nature 256:495-497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026-2030), and the EBV-hybridoma technique (Cole et al., 1985, Monoclonal Antibodies and Cancer Therapy, Alan R. Liss, Inc., pp. 77-96).

Monoclonal antibodies for use in this invention can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

Chimeric, single chain and humanised antibodies may also be used as binding agent in this invention. Techniques for the production of chimeric antibodies (Morrison et al., 1984, Proc. Natl. Acad. Sci., 81:6851-6855; Neuberger et al., 1984, Nature, 312:604-608; Takeda et al., 1985, Nature, 314:452-454; U.S. Pat. No. 4,816,567) comprise splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Techniques described for the production of single chain antibodies can be found in U.S. Pat. No. 4,946,778: Bird, 1988, Science 242:423-426; Huston et al., 1988, Proc. Natl. Acad. Sci. U.S.A. 85:5879-5883; and Ward et al., 1989, Nature 334:544-546. Techniques for making humanized monoclonal antibodies are described in U.S. Pat. No. 5,225, 539 (incorporated in its entirety herein by reference).

Antibody fragments for use in this invention (which fragments recognise specific epitopes) can be generated by known techniques. For example, such fragments include but are not limited to: the F(ab')2 fragments which can be produced by pepsin digestion of the antibody molecule and the Fab fragments which can be generated by reducing the disulfide bridges of the F(ab')2 fragments. Alternatively, Fab expression libraries can be constructed (Huse et al., 1989, Science, 246:1275-1281) to allow rapid and easy identification of monoclonal Fab fragments with the desired specificity.

The present invention may exploit a monoclonal anti-IgG, monoclonal anti-IgG$_1$, a monoclonal anti-IgG$_3$, and a monoclonal anti-C3. When anti-IgG is included, this is conveniently a (polyclonal or monoclonal) anti-IgG. A blend of these probes may also be used to give the same result, without differentiation of the type of antibody bound.

All forms of antibody suitable for use in this invention, including those described above, shall be collectively referred to as "antibodies".

The binding agents, including any antibodies, used in this invention may be bound or immobilised to or on a substrate. Any conventional substrate may be used in this invention. Suitable substrates include those that are rigid or semi-rigid in nature. For example suitable substrates may include, membranes, filter, chips, slides, wafers, fibers, magnetic or nonmagnetic beads, gels, tubing, plates, polymers, microparticles and/or capillaries. The substrate can have a variety of surface forms, such as wells, trenches, pins, channels and pores, to which the binding agents and/or antibodies are immobilised/bound. The substrates may be planar in nature having an upper flat surface upon which components of the methods of this invention may be immobilised and/or bound. As described in more detail below and depending on methods used to affect the detection of bound sensitised red blood cells (erythrocytes), the substrate surface architecture may be formed and adapted to improve or facilitate fluorescent based detection methods. Substrates of this type are described in WO02/059583 and WO03/023377. Accordingly, substrates for use may be optically transparent.

Suitable substrates may include those comprising glass, silicon, silicon oxide, metals and metal oxides either bare or functionalised with functional polymers such as, for example, glycidoxypropyltriethoxysilane, poly-l-lysine, am inopropylsilane, carboyxsilane, hydrogels and polymer-brushes, self-assembled monolayers of e.g. functionalised alkyl thiols. A suitable substrate for use in this invention may comprise silane based coating for example, a silane compound with a hydrophobil linkage and functional group with the ability to bind to biological molecules of interest.

Binding agents and/or antibodies for use in this invention may be bound or immobilised to a substrate in an array. As used herein the term "array" refers to a generally ordered arrangement of bound probes (for example binding agents and/or antibodies), that specifically bind to sensitised red blood cells (or rather the antibodies which coat/sensitise the red blood cells), on a substrate such as glass.

Typically the array may be in the form of a series of regularly spaced apart delimited areas to which the binding agents and/or antibodies are bound. Such substrate bound antibody arrays may be commonly described as "antibody chips".

The antibodies may be arranged on, for example, a flat or spherical substrate referred hereto as a "chip". The methods of this invention may exploit a single type of binding agent or antibody or a plurality of different antibodies. Thus at least one but perhaps at least 2, 3 or 4 different antibodies may be bound to the surface of the substrate. Moreover, each specific antibody may be provided in a number of dilutions and/or repeated a number of times (e.g. 3-10 times), in order to further minimise any false positive or negative reactions which may occur, when carrying out a method of detection.

Substrates used to prepare "antibody chips" for use in this invention may comprise small planar substrates. Suitable planar substrates may be any suitable size. For example a planar substrate for use in this invention may be anywhere between about 5 mm and about 100 mm in length and about 5 mm to about 50 mm in width. For example, a suitable planar substrates may be about 76 mm by about 26 mm or about 12.5 mm by about 7.9 mm in size.

The binding agent or antibody may be applied to the substrate by spotting or printing. Suitable known techniques, include those described by Michael J. Heller, Annual Review of Biomedical Engineering, 2002 Vol. 4: 129-153. DNA Microarray Technology: Devices, Systems and Applications and Angenendt, P.; GINler, J.; Murpy, D.; Lehrach, H.; Cahill, D. J. Anal. Biochem., 2002, 309, 252-260 Angendt, P.; GINler, J.; Sobek, J.; Lehrach, H.; Cahill, D. J. Chromatogr. A, 2003 100, 997-104.

Spotted or printed spots of binding agent/antibody may be less than 1 mm in diameter, such as less that 500 µm or 100 µm in diameter or between about 50 µm and about 1000 µm in diameter. In this manner 10 s to 1000 s of individual and discrete binding agent/antibody spots may be provided on the surface of any given substrate.

For the avoidance of doubt any one location or spotted/printed spot on a substrate of this invention may comprise a single binding agent/antibody type or two or more binding agent/antibody types.

Various procedures are well known in the art for immobilising binding agents and/or antibodies of the type described herein, to the surface of a substrate. For example, electrostatic binding may be used to immobilise antibodies. Other methods which may be used to immobilise or attach a binding agent or antibody to a surface include hydrophobic/hydrophillic interactions, chemical interactions, and amine coupling. Binding agents and antibodies may be adsorbed directly onto gold containing substrates via sulphur containing amino acids (cysteine, methionine), or through binding via alkanethiols which comprise functional groups to interact with the binding agents, previously bound to the gold containing substrate.

Areas of the substrate surface which are not provided with binding agent and which could provide non-specific binding sites are desirably treated with blocking agents in order to prevent any non-specific binding of antibodies, complement factors (and other plasma derived components), red blood cells or sensitised RBCs. Suitable blocking agents are well known in the art and may comprise albumin or serum (free of undesirable antibodies such as blood group antibodies, anti-IgG antibodies or those that could interfere with any test probe interactions on the same microarray), non-fat milk protein, casein, bovine serum albumin (BSA) and the like. The blocking agents may be formulated or prepared for use with a suitable buffer.

For example, a suitable blocking agent may comprise, 1% w/v bovine serum albumin (BSA) (ID Bio, France) in Phosphate Buffered Saline (PBS) (0.15 M sodium chloride, 2.632 M Phosphate Buffer Stock Solution (Quotient, Scotland), pH 7.0).

Optionally coated substrates prepared for use in this invention may be stored for use as dried substrates. Additionally or alternatively, the substrates may be stored at ambient temperature or under refrigerated/freezing conditions.

In view of the above, the crossmatching methods of this invention may be conducted in a microarray format. Microarray crossmatching assays represent efficient and effective alternatives to conventional crossmatch testing. Moreover, microarray crossmatching assays may be readily integrated into other tests (for example other microarray tests) important in blood processing—including, for example, blood group phenotyping for multiple antigens on the surface of the red blood cell (erythrocyte).

Following incubation under conditions which permit binding between sensitised red blood cells and the immobilised binding agents and/or antibodies, unbound red blood cells may be removed by, for example, washing.

The presence of the captively held (bound) sensitised red blood cells (erythrocytes) may be detected by means of various techniques known in the art such as, for example, secondary labelling detection which may exploit fluorescent, chemiluminescent conjugated antibodies.

Fluorescence may be detected by any suitable photo-detector known in the art, such as a spectrophotometer or digital imaging device such as, for example a CCD image sensor (in the form of a CCD camera) or a CMOS sensor. Conveniently there may be used a simple flatbed scanner with the red blood cell (erythrocyte) binding being detected by the scanner and the intensity thereof given a visual output for interpretation or a numerical value for purposes of interpretation and data processing.

Conveniently bound sensitised red blood cells may be detected by means of the autofluorescence of the RBCs as described in C J Campbell et al., 2006. Detection by autofluorescence has the particular advantage of avoiding the need for the use of any labelling and providing a particularly simple form processing. In more detail the RBCs may be irradiated or excited with light of wavelength about 420 nm, 488 nm, 543 nm or 580 nm, and fluorescent emission detected at a longer wavelength such as 530 nm if excited at 488 nm or 570-585 nm if excited at 543 nm.

Thus, in this invention, bound sensitised red blood cells (erythrocytes) may be detected by a fluorescent signal or by image generation following scanning using, for example, a flatbed scanner.

It will be appreciated that by knowing the position of each specific antibody on the substrate, it is possible to determine whether or not donor red blood cells erythrocytes have been sensitised by antibodies present in patient plasma samples. For the avoidance of doubt, compatible donor units yield negative results (no sensitisation thus no cells bound) whereas incompatible donor units yield positive results (sensitisation, therefore positive detection of bound sensitised red blood cells). One of skill in this field will understand that using appropriate electronics and software, any device can be programmed to "know" or recognise the identity and location of specific antibodies on the surface of the substrate and to correlate this with signals generated, so that a particular binding can be determined and identified to the tester. Additionally, statistical software may be included so as to combine and formulate the results from the various repetitions and/or dilutions of the antibodies provided on the substrate. In this manner, the signals obtained from a multiplicity of specific antibody spots may be factored together and a statistically significant result displayed to the tester.

The methods of this invention may include one or more controls. For example, a positive control may be used confirm the addition of red blood cells. A positive control may comprise anti-erythrocyte antibodies. The anti-erythrocyte antibodies may be immobilised and/or spotted/printed onto a substrate as described in more detail above.

It should be understood that while the present invention has been described with reference to crossmatching assays, the methods described herein, in particular the processing of a cell mix into (sensitised) red blood cell and liquid phases without the use of centrifugation and/or wash steps, may be exploited in a number of different immunological assays. For example, any assay which requires the incubation of a source of antibodies and red blood cells (erythrocytes) and the subsequent detection of sensitised red blood cells (erythrocytes: forming during incubation between the antibody source and the red blood cells), may benefit from the procedures described herein. Thus the invention may provide a means of providing red blood cells for use in a method of detecting sensitised red blood cells the method comprising incubating red blood cells and a composition capable of sensitising red blood cells (for example a composition comprising antibodies and/or complement components, for example plasma or serum) under conditions which facilitate the sensitisation of the red blood cells and the settling under gravity of the red blood cell component; and removing the liquid phase (or supernatant) and/or removing at least a sample of the red blood cells.

Further preferred features and advantages of the invention will appear from the following detailed Examples given by way of illustration.

DETAILED DESCRIPTION

FIG. 1: Diagrammatic representation of a single array (12×12 grid of spots) showing the antibodies printed. 16 arrays were printed on each slide in a 2×8 format. Black spots indicate antibody printed (in triplicate) and white spots indicate 50% glycerol/PBS printed as negative spots.

Figure 2:
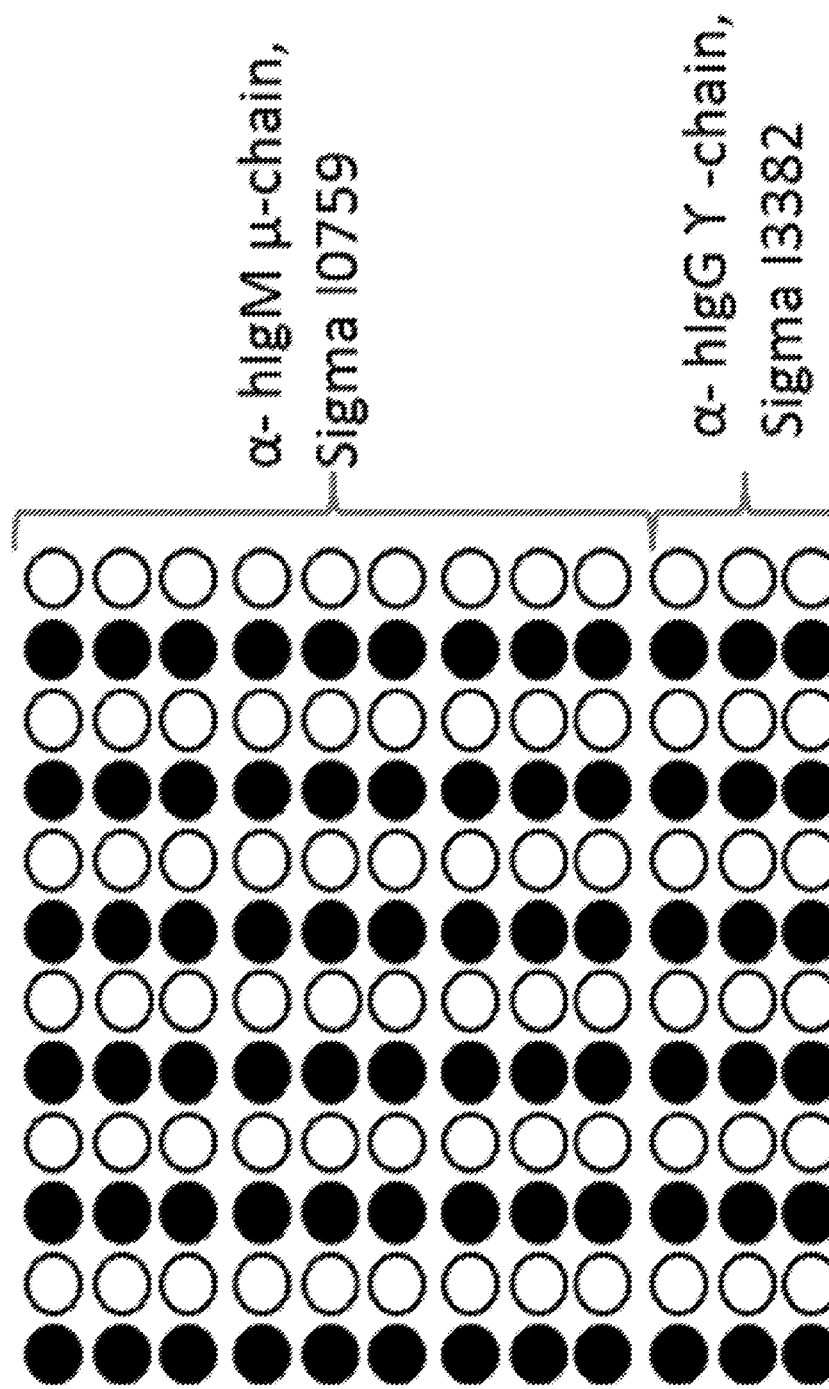

FIG. 2: Diagrammatic representation of a single array (12×12 grid of spots) showing the two antibodies printed. α-hIgM was printed at 518 μg/mL and α-hIgG at 301 μg/mL. 16 arrays were printed on each slide in a 2×8 format. Black spots indicate a positive cell binding response and white spots indicate 50% glycerol/PBS printed as negative spots which should not bind any cells.

Figure 3:
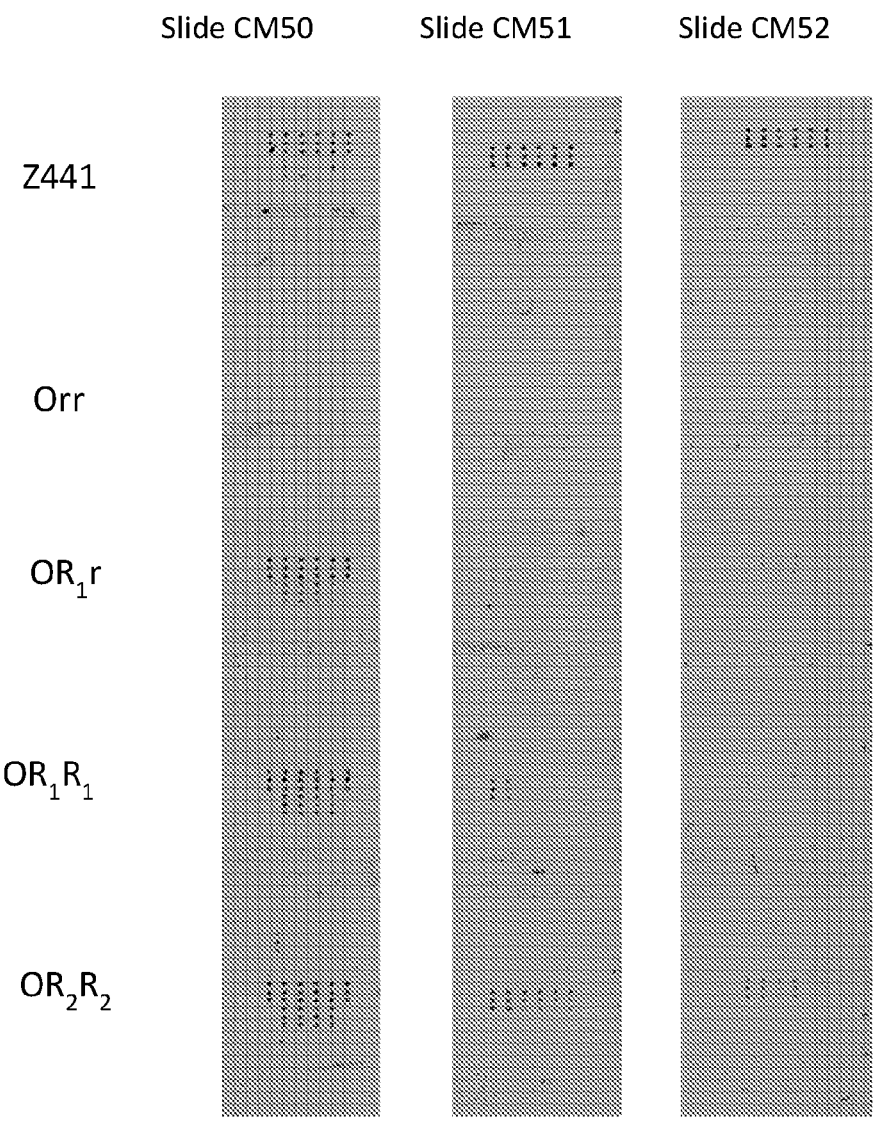

FIG. 3: Image of slides CM50, CM51 and CM52 showing the results for Orr, $OR_1r$, $OR_1R_1$ and $OR_2R_2$ cells sensitised with anti-D plasma for 30 minutes using the tube, glass slide or plate technique respectively. Also shown are the results for the positive control cells (Z441, IgG Sensitised Cells).

FIG. 4: Image of slides CM60 and CM61 showing the results for $OR_1r$, $OR_1R_1$, $OR_2R_2$ and Orr cells sensitised with anti-D plasma for 30 minutes using the tube or glass slide technique respectively. Also shown are the results for the positive control cells (Z441, IgG Sensitised Cells) and the agglutination grading results from the indirect agglutination testing using AHG (AHG result=reference technique).

Figure 5:
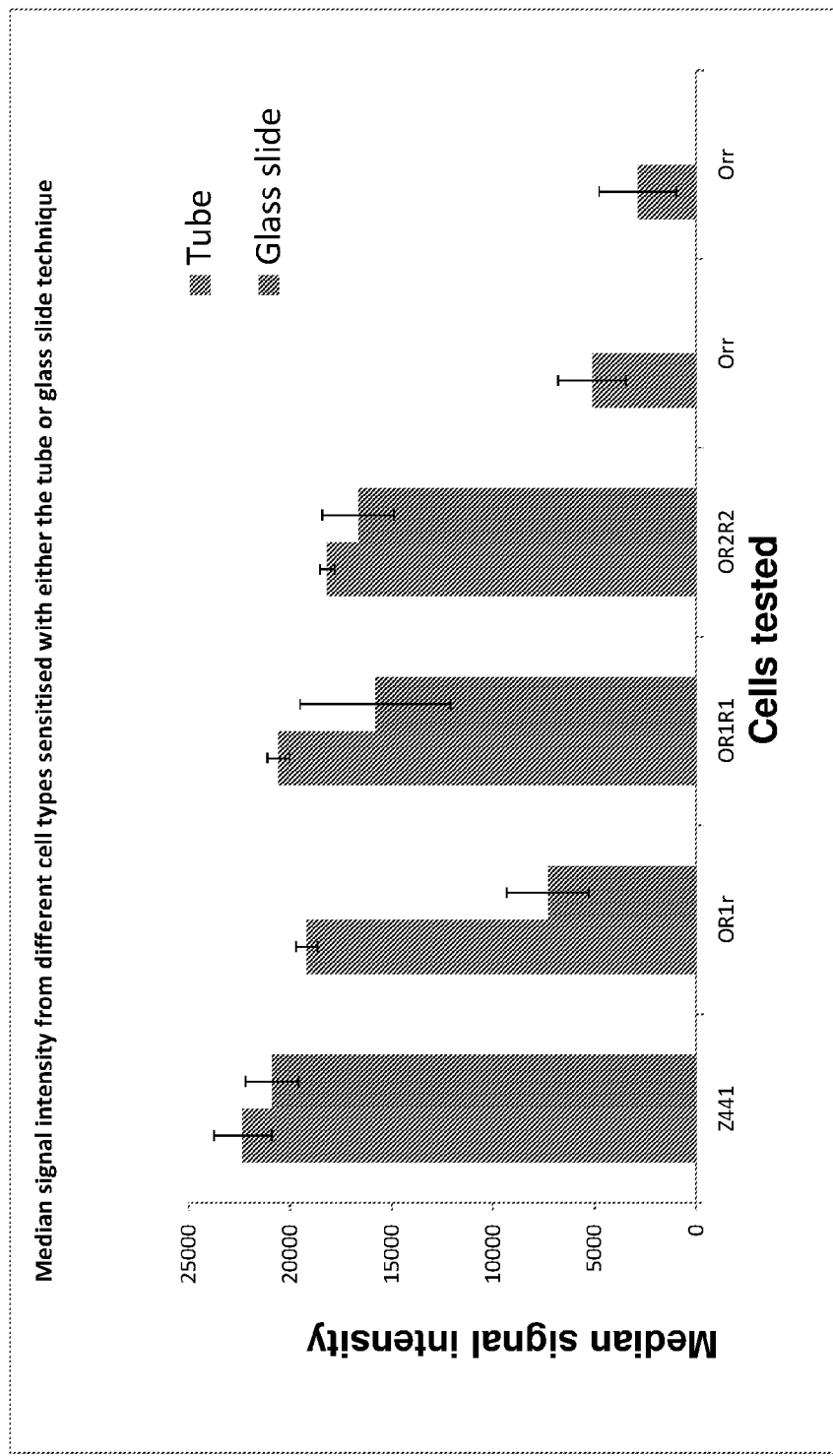

FIG. 5: Data generated from images shown in FIG. 4, showing the median signal intensity for the cells tested to the α-hIgG printed in the array. The results for the tube or glass slide technique are shown with the standard deviation of the median signal intensity plotted.

Figure 6A:
Figure 6B:
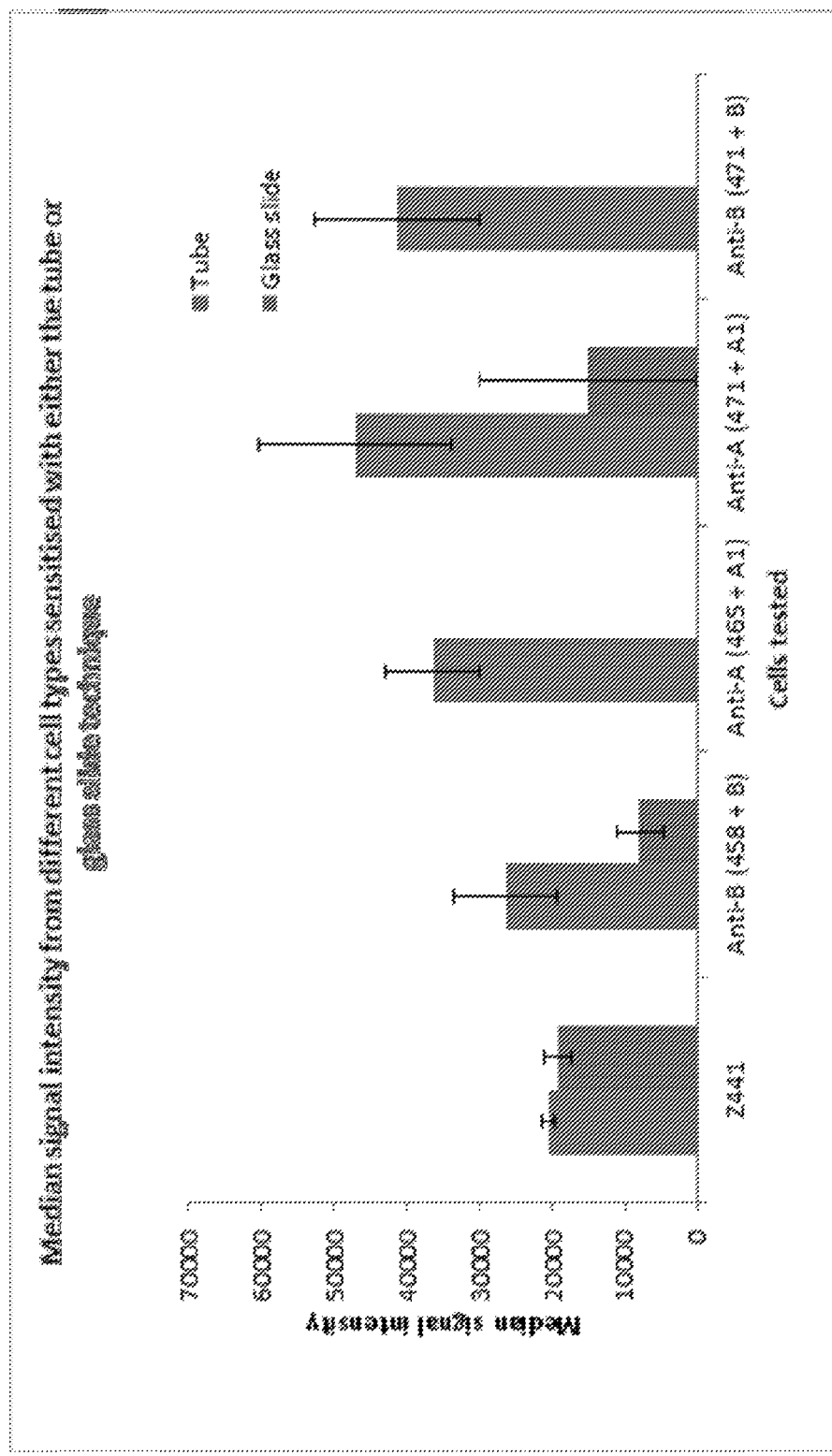

FIGS. 6 a & b: Images of slides CM62 and CM63 showing the results for Anti-A and Anti-B plasmas tested with $A_1$ or B cells using the tube or glass slide techniques respectively. Also shown are the results for the indirect test using AHG in tubes with the agglutination grading result down the left hand side of the figure. Note that this testing was performed manually and, therefore, some disruption may be evident that would be reduced/eliminated when automated methods are employed.

Figure 7:
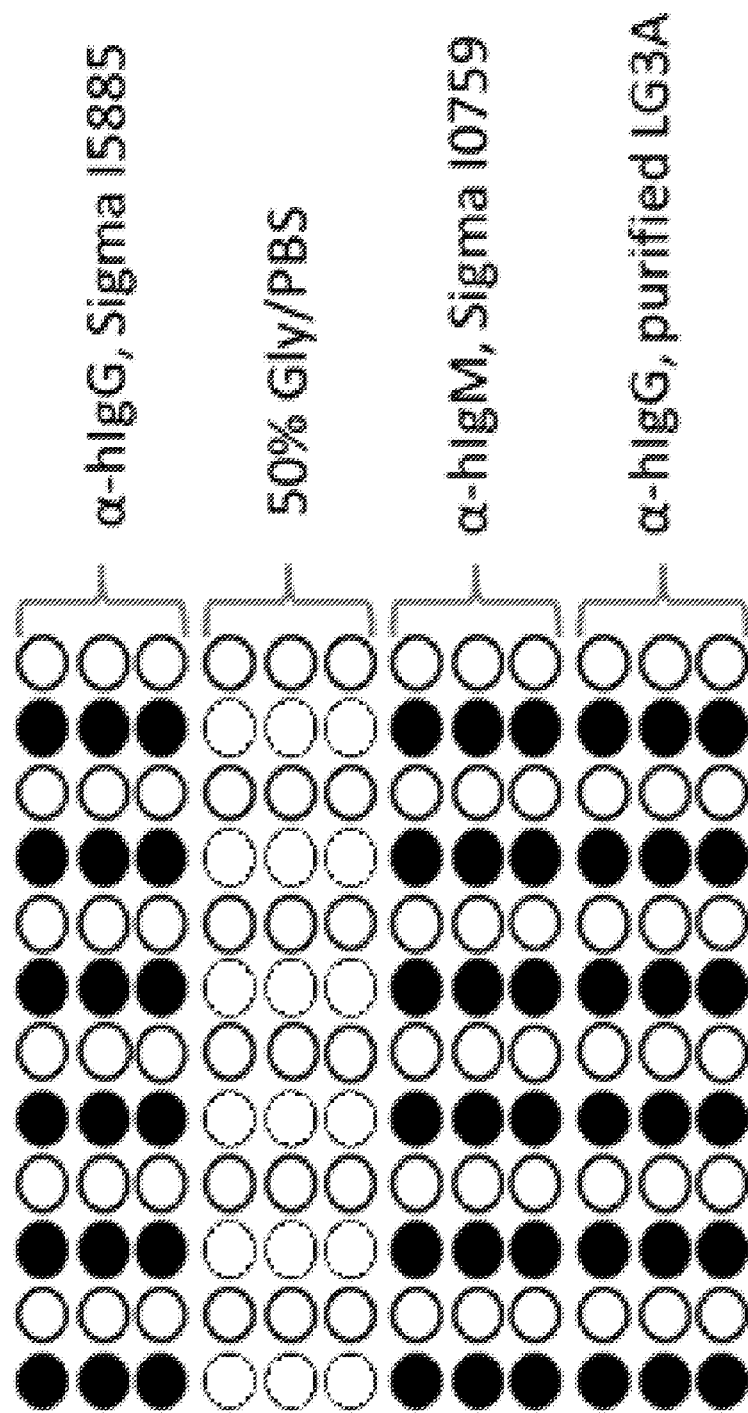

FIG. 7: Diagrammatic representation of a single array showing the antibodies printed. Anti-human IgM was printed at 518 μg/mL and α-hIgG at 301 μg/mL. 16 arrays were printed on each slide in a 2×8 format. Black spots indicate a positive cell binding response and white spots indicate 50% glycerol/PBS printed as negative spots which should not bind any cells.

Figure 8:
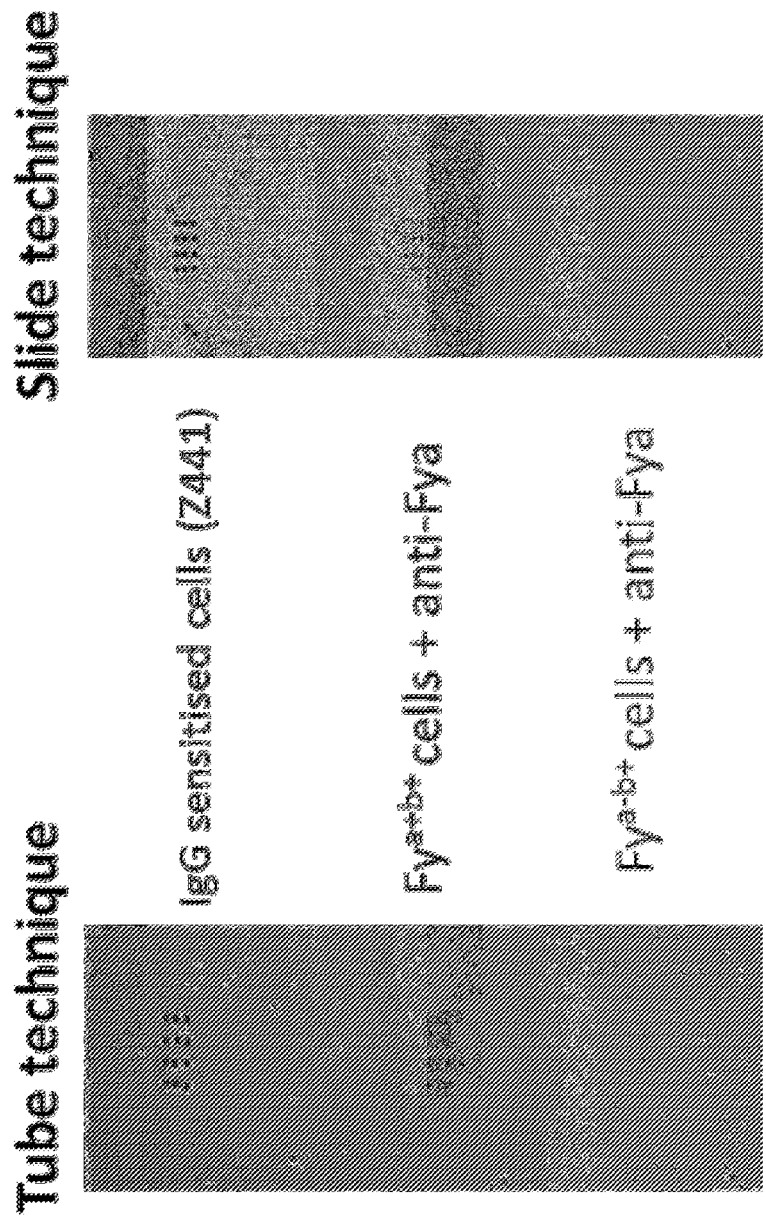

FIG. 8: Image of slides 1 and 2 showing the results for Fy(a+b+), Fy(a+b−) and Fy(a−b+) cells sensitised with monoclonal anti-$Fy^a$ for 30 minutes using the tube or glass slide technique. Also shown are the results for the positive control cells (IgG Sensitised Cells, Z441).

Figure 9:
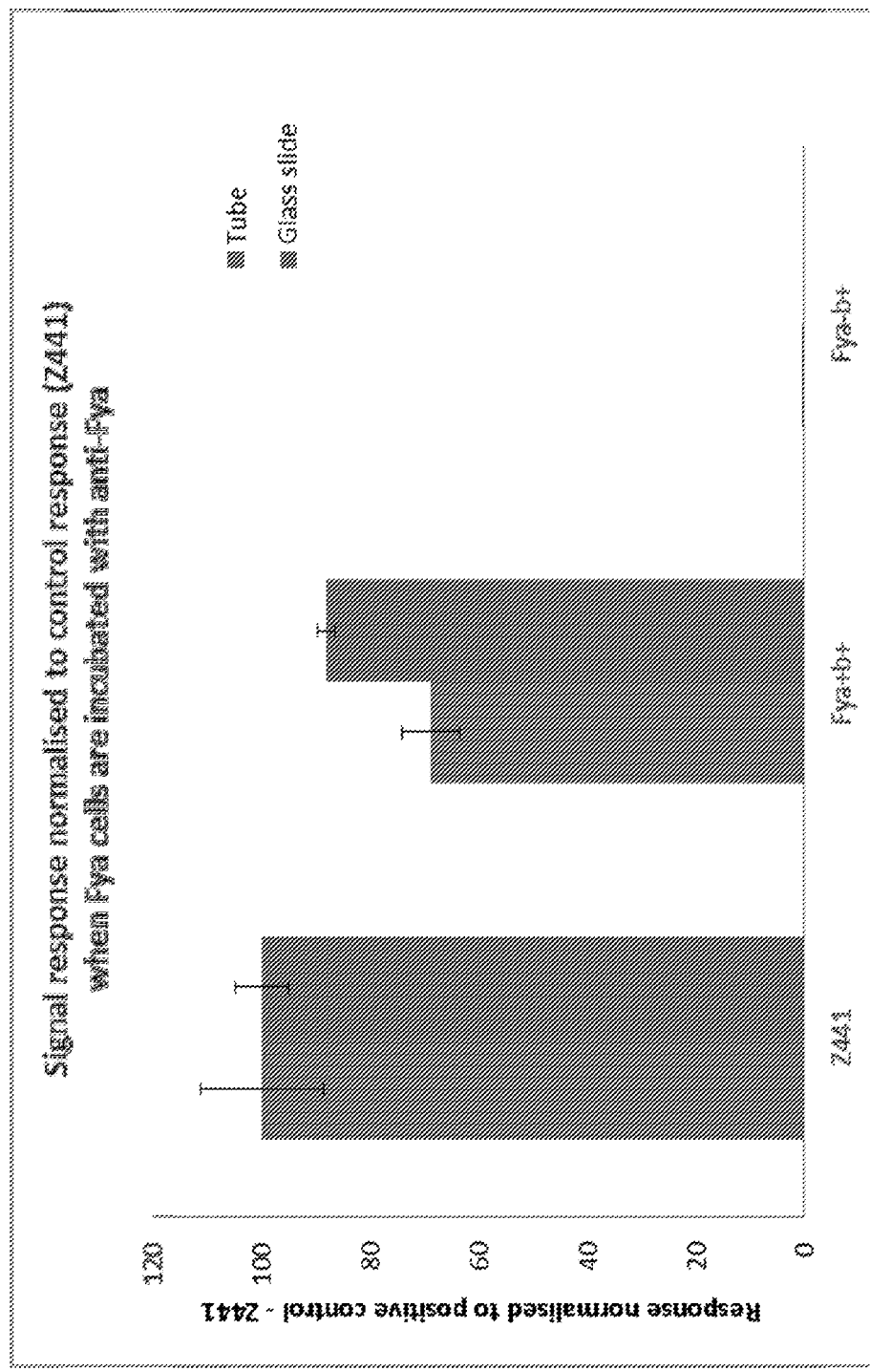

FIG. 9: Data generated from images shown in FIG. 2, showing the signal response which has been normalised to the median signal intensity for the positive control cells (Z441) tested on the slide. Because the results for the tube and slide technique were performed on separate slides, this accounts for any differences in signal across arrays on different slides. The results for the tube or glass slide technique are shown. The IgG sensitised cells (Z441) demonstrate the control signals. When using the monoclonal Anti-$Fy^a$, good binding is seen by both techniques. The Fy(a−b+) cell shows low or negative reactivity as expected. In this way we can see that the sample containing Anti-$Fy^a$ is incompatible with Fy(a+) cells and negative with Fy(a−), demonstrating the principle of the crossmatch.

EXAMPLE 1—PREPARATION OF PROTEIN MICROARRAYS

Coated slides obtained from Schott were used as the substrate. The binding agent antibody probe samples to be spotted were prepared in 50% Glycerol/50% PBS.

The slides were printed using an Arrayjet Sprint Arrayer (Arrayjet) with a 12 sample Jetspyder. Replicates of each sample were printed on each slide separated by negative control spots of 50% glycerol/PBS—see FIG. 1. All slides were printed within a relative humidity between 40-60%, and at an ambient temperature (20-23° C.). Printed probes were left to immobilise in the humidified atmosphere for 30 minutes prior to being stored in a box at 2-8° C. in the dark for at least 24 hours.

Further arrays were printed for the testing of anti-A and anti-B plasmas which are shown in FIG. 2.

EXAMPLE 2—WASHING OF CELLS PRIOR TO USE IN EXPERIMENTS

All cell types were suspended in LISS or washed into LISS (low ionic strength saline)—other diluents may be used, including, for example PBS, Modified Alsevers, and variations thereof. Moreoever, cells need not be washed—rather a small volume of cells may be removed from the donor sample (which has perhaps been centrifuged) directly into LISS buffer. Where washing was used, cells were centrifuged three times at 3000 rpm for 2 minutes using a Thermo Centra CL2 centrifuge with the supernatant removed each time and replaced with ~4 mL PBS. After the final centrifugation, one wash in LISS was performed before re-suspending the cells to 2% HCT in LISS.

For experiments where different haematocrits of cells were detected, cells were prepared at 8% HCT (160 μL of the resultant cell pellet was added to 1000 μL of LISS). The 8% HCT cells were then diluted further in LISS to achieve the required percentage haematocrit.

EXAMPLE 3—INDIRECT AGGLUTINATION TESTING OF SENSITISED CELLS (CONVENTIONAL METHOD, REFERENCE TECHNIQUE)

Volumes (40 μL or 80 μL) of the cell suspension were incubated with 80 μL of neat or diluted plasma in a tube. The resulting mix was incubated in a water bath at 37° C. In this example, the mix was incubated for 30 or 45 minutes but shorter or longer times could be used. Under these conditions, the red blood cells are sensitised. Where plasma was diluted, the diluent may be the same as that used for the red cells suspension—other suitable diluents can be used.

Following the incubation period, cells were washed using the nW program on a DiaCent 2000 Cell washer (×4 washes with PBS, then centrifugation at 1000 g). Two drops of AHG were added and the tubes were finally centrifuged (1000 g, 10 secs) and agglutination of cells read over a light box.

EXAMPLE 4—TUBE TECHNIQUE FOR SENSITISING CELLS

Volumes (240 μL—or matched with volume of plasma) of cell suspension were incubated with 480 μL neat or diluted plasma. Plasma was diluted in either PBS or LISS. Tubes were incubated at 37° C. (for 30 or 45 minutes—longer or shorter times may be used). Following the incubation period, cells were washed using a DiaCent 2000 Cell washer (×4 washes with PBS and a final centrifugation). Cells were then resuspended in 240 μL 2% BSA/LISS prior to adding to the arrays as described in Example 7.

EXAMPLE 5—GLASS SLIDE TECHNIQUE FOR SENSITISING CELLS (REMOVAL OF UNBOUND ANTIBODY BY REMOVING PLASMA/SUPERNATANT AND RESUSPENSION)

A blank slide (Schott, Glass B) was fitted into a Grace-Bio 16-well manifold. Blocking solution (2% BSA/PBS) was warmed to approximately 37° C. and slides were blocked by addition of 160 μL of blocking solution to each well and incubated at 37° C. with shaking (350 rpm) on a Grant Bio Thermoshaker for 15 minutes (with plastic cover). After blocking the solution was removed and 80 μL of (optionally washed) cells were incubated with 160 μL plasma. The slide was incubated stationary for 30 or 45 minutes at 37° C. Incubation time was dependent on the experiment being performed.

Following the incubation (substantially) the whole volume of liquid (or liquid phase) was removed quickly from the top right hand corner of each well.

The remaining cells were re-suspended in 240 μL 2% BSA/LISS prior to adding to the arrays as described in Example 7.

EXAMPLE 6—PLATE TECHNIQUE FOR SENSITISING CELLS (REMOVAL OF SENSITISED ERYTHROCYTES FROM PLASMA/SUPERNATANT AND THEN RESUSPENSION)

Volumes (40 μL) of washed cells were incubated with 80 μL plasma stationary in a U-bottomed 96 well plate for 30 or 45 minutes at 37° C. using a Grant Bio Thermoshaker. For investigating the change in total volume, 80 μL of cells were incubated with 160 μL plasma. Incubation time was dependent on the experiment being performed. Following the incubation time 4 μL of the cell pellet from the bottom of the well was removed to a separate well containing 100 μL 2% BSA/LISS. The cells were re-suspended prior to adding to the arrays as described in Example 7.

EXAMPLE 7—PROCESSING OF ARRAYS

Printed array slides were removed from 2-8° C. storage and fitted into Grace-Bio 16-well manifolds ensuring both central and straight alignment of the arrays in each well, secured using the metal clips and fitted into a Proplate tray (3 slide type). Slides were returned to storage at 2-8° C. until immediately prior to use. Blocking solution (2% BSA/PBS) was warmed to approx. 37° C. Slides were blocked by adding 160 μL of blocking solution to each well and incubated at 37° C. with shaking at 350 rpm on a Grant Bio PHMP Thermoshaker for 15 minutes (with plastic cover).

After blocking the solution was removed and 120 μL of sensitised cells (from Examples 4-6) were slowly pipetted into the left hand side of each appropriate well.

Slides were incubated stationary at 37° C. for 15 minutes (with plastic cover). Following incubation, the whole Proplate tray containing slides was dipped into a tub of PBS. Suction may be used to remove the PBS and any other fluid in the wells.

Slides were carefully removed from the Grace-Bio manifold and transferred to a slide holder and submerged into fresh PBS. Optionally slides may be fixed by immersion in 0.1% gluteraldehyde/PBS for 10 minutes at 2-8° C., or more conveniently the PBS is removed by suction and analysis performed directly using the flatbed scanner. This was followed by a final wash in water before centrifuged to dryness. Slides stored in a dust-free dark place until scanning.

EXAMPLE 8—DATA EXTRACTION AND ANALYSIS

Slides were scanned using a flatbed scanner to capture a high resolution image and saved as a 16-bit TIFF file.

Where red blood cells are bound to antibodies a black spot is evident.

Numerical data was extracted from the microarrays using an in-house generated algorithm that can quantify the signal intensity.

A text input file was self-generated using microarray column and row positions to determine identity and location of each probe. This was used to generate an array list that was loaded once the microarray grid settings had been set up. Once the grid and the array list had been generated, the data was extracted to a text file. This process gave the median fluorescence intensity value from the centre of each spot and a median background value from the entire background area of the slide. This information was collected into an Excel worksheet.

For each spot the background value was subtracted from the spot intensity value. For each slide the signal intensity values from each different scan setting were collated into one worksheet.

Once the best data scan had been selected it was processed as follows. Unwanted data were removed from the worksheet to leave only one value per spot on the microarray (the spot intensity value minus the background value for each spot). The negative control values were used to calculate a 'noise' value—the mean plus two standard deviations of the negatives (mean+2 sd). This value represents non-specific binding (NSB). The value for each spot was divided by the mean+2 sd of the negative controls to give a signal-to-noise ratio (S/N). Values over one can be considered significant. The median of the S/N was calculated for the replicate spots of each sample.

Using Microsoft Excel the processed data was analysed as appropriate. Bar charts were used throughout to analyse data. The Y-axis on the bar charts represents the S/N median for the sample.

Where error bars were included, the standard error for each sample was calculated as follows. The standard deviation of the replicates of each sample was calculated (this was performed on S/N ratios or actual values). The standard deviation was divided by the square root of the number of replicates of the sample to give the standard error.

Supplementary Data

Protein Microarrays were prepared as per Example 1 above. Cells were washed prior to experiments as per Example 2 above. Indirect agglutination testing of sensitised cells (conventional method: reference technique) was performed as per Example 3 above. The "tube technique" for preparing sensitised cells was performed as per Example 4 above. The "glass slide technique" for sensitising cells (removal of unbound antibody (without centrifugation/washing) by removing plasma/supernatant and re-suspension) was performed as per Example 5 above. Assays were processed as per Example 7 above.

Data Extraction and Analysis

As per Example 8 of original patent except that the Y-axis on the bar charts represents the S/N median for the sample normalised to the positive control (Z441) result and calculated as a percentage.

Where error bars were included, the % Coefficient of Variance associated with the value for each sample was calculated as follows. The % CV of the replicates of each sample was calculated (this was performed on S/N ratios or actual values). The mean value was standard deviation and then multiplied by 100 to give the % CV.

REFERENCES

Robb. J. S., Roy, D. J., Ghazal, P., Allan, J. and Petrik, J. (2006). "Development of non-agglutination microarray blood grouping" Transfusion Medicine. 16, 119-129.

Campbell, C. J., O'Looney, N., Chong Kwan, M., Robb, J. S., Ross, A. J., Beattie, J. S., Petrik, J. and Ghazal, P. (2006). "Cell Interaction Microarray for Blood Phenotyping" Analytical Chemistry. 78, 1930-1938.

British Committee for Standards in Haematology; Milkins, C., et al. (2013). Guidelines for pre-transfusion compatibility procedures in blood transfusion laboratories. Transfusion Medicine 23, 3-35.

Issit, P. D. and Anstee, D. J. (1998) Applied Blood Group Serology. Fourth Edition. Montgomery Scientific Publications.

The invention claimed is:

1. A method of crossmatching first and second blood samples, said method comprising:
   providing plasma and/or serum from a first blood sample;
   contacting the plasma and/or serum with red blood cells from a second blood sample to provide a plasma and/or serum/red blood cell mix;
   incubating the plasma and/or serum/red blood cell mix under conditions which permit sensitisation of the red blood cells with any anti-blood group antigen antibodies present in the plasma and/or serum of the first blood sample;
   separating the red blood cells from a liquid phase; and
   contacting the red blood cells with an agent capable of binding sensitizing anti-blood group antigen antibodies;
   wherein the separation of the red blood cells from the liquid phase takes place without centrifugation and the detection of sensitised red blood cells bound to the agent capable of binding antibodies indicates that the first blood sample is incompatible with the second blood sample.

2. The method of claim 1, wherein the plasma and/or serum is prepared from whole blood.

3. The method of claim 1, wherein the plasma and/or serum is obtained from, provided by, or derived from, a patient who is to receive a blood transfusion.

4. The method of claim 1, wherein the red blood cells are obtained from, provided by, or derived from donor blood.

5. The method of claim 1, wherein the sensitisation of the red blood cells occurs through binding between antibodies present in the plasma and/or serum and antigens of the red blood cells.

6. The method of claim 5, wherein the antigens are blood group antigens.

7. The method of claim 1, wherein the plasma and/or serum/red blood cell mix is incubated at about 30-40° C. for about 10 seconds to several hours.

8. The method of claim 1, wherein the plasma and/or serum/red blood cell mix is incubated at about 37° C. for about 5 min, about 10 min, about 15 min, about 20 min, about 25 min or about 30 min.

9. The method of claim 1, wherein the plasma and/or serum/red blood cell mix is incubated under conditions which permit the separation of the red cell component of the cell mix from the liquid phase of the cell mix.

10. The method of claim 1, wherein the plasma and/or serum/red blood cell mix is incubated under conditions which facilitate the settling of the red blood cells to form a pellet.

11. The method of claim 1, wherein separating the red cells from a liquid phase further comprises removing the supernatant to leave only the red blood cells and/or removing a sample of the pelleted red blood cells.

12. The method of claim 11, wherein the supernatant is removed by pipetting, decanting and/or aspiration.

13. The method of claim 1, wherein before being brought into contact with agents capable of binding antibodies, the red blood cells are re-suspended in a suitable buffer.

14. The method of claim 1, wherein the agents capable of binding antibodies are selected from the group consisting of:
   (i) antibodies or antigen binding fragments thereof, with specificity for one or more antibody isotypes;
   (ii) small molecule antibody mimetics;
   (iii) aptamers;
   (iv) nucleic acid ligands
   (v) receptors from other cells; and
   (vi) Lectins.

15. The method of claim 1, wherein the agents capable of binding antibodies are bound or immobilised to or on a substrate.

16. The method of claim 15, wherein the substrate is a functionalised and/or coated substrate.

17. The method of claim 15, wherein the substrate is functionalised and/or coated with one or more compounds selected from the group consisting of:
   (i) a functional polymer;
   (ii) glycidoxypropyltriethoxysilane;
   (iii) poly-l-lysine;
   (iv) aminopropylsilane;
   (v) carboyxsilane;
   (vi) hydrogels;
   (vii) polymer-brushes, self-assembled monolayers of functionalised alkyl thiols;
   (viii) silane based coating; and
   (ix) a silane compound with a hydrophobil linkage and functional group with the ability to bind to biological molecules of interest.

18. The method of claim 1, wherein the agents capable of binding antibodies are bound or immobilised to a substrate in an array.

19. The method of claim 9, wherein the agents capable of binding antibodies are applied to the substrate by spotting or printing.

20. The method of any one of claim 6, wherein the substrate is subjected to a blocking protocol to prevent areas of the substrate which are not provided with agents capable of binding antibodies from acting as non-specific binding sites.

21. The method of claim 16, wherein the functionalized and/or coated substrates are stored for use as dried substrates.

22. The method of claim 1, wherein the method is conducted in a microarray format.

23. The method of claim 1, wherein the method is combined with one or more other tests and/or microarray tests.

24. The method of claim 23, wherein the one or more other tests and/or microarray tests are selected from the group consisting of blood group phenotyping tests and/or blood borne disease tests.

25. The method of claim 1, wherein following incubation under conditions which permit binding between sensitised red blood cells and agents which bind antibodies, unbound red blood cells are removed by washing.

26. The method of claim 1, wherein the detection of sensitised red blood cells bound to the agents capable of binding antibodies comprises the use of secondary labelling detection techniques and/or fluorescent, chemiluminescent conjugated antibodies and/or red blood cell autofluorescence.

27. The method of claim 1, wherein the detection of sensitised red blood cells bound to the agents capable of binding antibodies comprises the use of a fluorescent signal and/or image generation.

28. The method of claim 1, wherein the method further comprises the use of one or more controls.

29. The method of claim 28, wherein the control(s) comprise a positive control to confirm the addition of red blood cells.

* * * * *

UNITED STATES PATENT AND TRADEMARK OFFICE
CERTIFICATE OF CORRECTION

PATENT NO. : 10,161,942 B2
APPLICATION NO. : 15/117035
DATED : December 25, 2018
INVENTOR(S) : Robb et al.

It is certified that error appears in the above-identified patent and that said Letters Patent is hereby corrected as shown below:

In the Specification

Column 9, Line 48: Please correct "GINler" to read -- Glökler --

Column 9, Line 50: Please correct "GINler" to read -- Glökler --

Signed and Sealed this
Twentieth Day of December, 2022

Katherine Kelly Vidal
*Director of the United States Patent and Trademark Office*